(12) United States Patent
Wang et al.

(10) Patent No.: US 8,520,922 B2
(45) Date of Patent: Aug. 27, 2013

(54) METHOD AND APPARATUS FOR DETECTION OF CARIES

(75) Inventors: Wei Wang, Minhang (CN); Liangliang Pan, Shanghai (CN); Lixing Shi, Changning (CN); Victor C. Wong, Rochester, NY (US)

(73) Assignee: Carestream Health, Inc., Rochester, NY (US)

( * ) Notice: Subject to any disclaimer, the term of this patent is extended or adjusted under 35 U.S.C. 154(b) by 242 days.

(21) Appl. No.: 13/144,308

(22) PCT Filed: Jan. 20, 2009

(86) PCT No.: PCT/CN2009/000078
§ 371 (c)(1),
(2), (4) Date: Jul. 13, 2011

(87) PCT Pub. No.: WO2010/083623
PCT Pub. Date: Jul. 29, 2010

(65) Prior Publication Data
US 2011/0275034 A1    Nov. 10, 2011

(51) Int. Cl.
*G06K 9/00*    (2006.01)
(52) U.S. Cl.
USPC .............................................. 382/128; 378/38
(58) Field of Classification Search
USPC ............ 382/100, 128, 129, 130, 131, 132, 382/133; 378/38, 168, 189, 190, 191; 362/572
See application file for complete search history.

(56) References Cited

U.S. PATENT DOCUMENTS

| | | | | |
|---|---|---|---|---|
| 5,386,448 | A * | 1/1995 | Tammisalo et al. | 378/38 |
| 6,231,338 | B1 * | 5/2001 | de Josselin et al. | 433/29 |
| 6,672,868 | B1 * | 1/2004 | Momot et al. | 433/29 |
| 7,668,355 | B2 * | 2/2010 | Wong et al. | 382/128 |
| 8,036,438 | B2 * | 10/2011 | Komiya | 382/128 |
| 8,406,859 | B2 * | 3/2013 | Zuzak et al. | 600/476 |
| 2004/0202356 | A1 * | 10/2004 | Stookey et al. | 382/128 |
| 2004/0240716 | A1 * | 12/2004 | de Josselin et al. | 382/128 |
| 2007/0099148 | A1 | 5/2007 | Wong et al. | |
| 2007/0248931 | A1 | 10/2007 | Wong et al. | |
| 2008/0063998 | A1 | 3/2008 | Liang et al. | |
| 2008/0232662 | A1 * | 9/2008 | Komiya | 382/128 |
| 2010/0303315 | A1 * | 12/2010 | Rohner et al. | 382/128 |

FOREIGN PATENT DOCUMENTS

| | | |
|---|---|---|
| CN | 1703162 | 11/2005 |
| JP | 06-065947 U | 9/1994 |
| WO | WO 2004/005895 | 1/2004 |
| WO | WO 2008/027323 | 3/2008 |
| WO | 2008/088672 A1 | 7/2008 |

OTHER PUBLICATIONS

International Search Report, mailed Oct. 1, 2009, from the PCT Offce re: Application No. PCT/CN2009/000078.
Luc Vincent, "Morphological Grayscale Reconstruction in Image Analysis: Applications and Efficient Algorithms," IEEE Transactions on Image Processing, vol. 2, No. 2, pp. 176-201, Apr. 1993.

* cited by examiner

*Primary Examiner* — Anand Bhatnagar

(57) ABSTRACT

A method for forming an enhanced image (60) of a tooth (20) making use of the tooth (20) fluorescence and/or reflectance effects, employs a morphological image processing technique, and reduces susceptibility to overall intensity variations in the image (60).

20 Claims, 5 Drawing Sheets

METHOD AND APPARATUS FOR DETECTION OF CARIES

CROSS REFERENCE TO RELATED APPLICATIONS

Reference is made to commonly-assigned copending U.S. patent application Ser. No. 11/468,883, filed Aug. 31, 2006, entitled METHOD FOR DETECTION OF CARIES, by Wong et al., and U.S. patent application Ser. No. 11/530,987, filed Sep. 12, 2006, entitled APPARATUS FOR CARIES DETECTION, by Liang et al., the disclosure of which is incorporated herein.

FIELD OF THE INVENTION

The invention relates to a method for dental imaging. More particularly, the invention relates to an improved method for early detection of caries using fluorescence and scattering of light.

BACKGROUND OF THE INVENTION

Dental caries is a major public health problem around the world. Dental caries has been identified as the single most common chronic disease of childhood. Despite the strides made in treating and preventing dental caries, significantly more needs to be done to further tackle the problem.

Dental caries is a chronic infectious disease. Earlier detection would reduce the ravages of the disease; it allows dental professionals to administer professional treatments to reverse the caries process rather than undertake more costly and less desirable restorative treatments.

Traditional methods for caries detection include visual examination and tactile probing with a sharp dental explorer device, often assisted by radiographic (x-ray) imaging. There are risks associated with conventional detection techniques, including the risk of damaging weakened teeth, spreading infection and exposure to x-ray radiation.

In response to the need for improved caries detection methods, there has been interest in improved imaging techniques that do not employ x-rays. One method that has been commercialized employs fluorescence, caused when teeth are illuminated with high intensity UV-blue light. This technique, termed quantitative light-induced fluorescence (QLF), operates on the principle that sound, healthy tooth enamel yields a higher intensity of fluorescence under excitation from some wavelengths than does de-mineralized enamel that has been damaged by caries infection. The strong correlation between mineral loss and loss of fluorescence for UV-blue light excitation is then used to identify and assess carious areas of the tooth.

In U.S. patent application Ser. No. 11/468,883, a method and apparatus that employs both the reflectance and fluorescence images of the tooth is used to detect caries. It takes advantage of the observed back-scattering for incipient caries and in combination with fluorescence effects, to provide an improved dental imaging technique to detect caries. The technique, referred to as fluorescence imaging with reflectance enhancement (FIRE), helps to increase the contrast of images over that of earlier approaches, and also makes it possible to detect incipient caries at stages when preventive measures are likely to take effect. Advantageously, FIRE detection can be accurate at an earlier stage of caries infection than has been exhibited using existing fluorescence approaches that measure fluorescence alone. The Application describes a down-shifting method (referred to as downshifting-FIRE) to generate the FIRE image.

SUMMARY OF THE INVENTION

It is an object of the present invention to provide a FIRE image generation method that has reduced sensitivity to illumination variation.

According to one aspect of the present invention, there is provided a method for forming an enhanced image of a tooth comprising:
a) obtaining fluorescence image data from the tooth by:
   (ai) directing incident light toward the tooth;
   (aii) sensing fluorescent emission from the tooth; and
   (aiii) storing a fluorescence image data value for each pixel position in the fluorescence image;
b) obtaining reflectance image data from the tooth by:
   (bi) directing incident light toward the tooth;
   (bii) sensing back-scattered reflectance light from the tooth; and
   (biii) storing a reflectance image data value for each pixel position in the reflectance image; and
c) combining each pixel in the fluorescence image data with its corresponding pixel in the reflectance image data by:
   (ci) calculating a regional maxima image data value from the reflectance image; and
   (cii) computing an enhanced image data value according to a difference between the fluorescence image data value and the regional maxima image data value; and whereby the enhanced image is formed from a resulting pixel array of enhanced image data values.

Preferably, the wavelength of the incident light for obtaining fluorescence image data is between 300 and 500 nm.

Preferably, the incident light is emitted from a white LED in step (b) and the incident light is emitted from a UV LED in step (a).

Preferably, the regional maxima image is calculated based on a morphological procedure employing grayscale reconstruction. More preferably, the morphological procedure is h-dome transformation, which comprises the following steps:
(1) calculating a Marker image from the Mask, which is a grayscale version of the reflectance image, by subtracting a predetermined value from the Mask;
(2) calculating the grayscale reconstruction of the Mask from the Marker;
(3) calculating the regional maxima image data value by subtracting the result of (2) from the Mask.

Preferably, the enhanced image data value computing step is performed by subtracting the regional maxima image data value from the fluorescence image data value.

Alternatively, the enhanced image data value computing step is performed by:
(i) multiplying the fluorescence image data value by a first scalar multiplier;
(ii) multiplying the regional maxima image data value by a second scalar multiplier;
(iii) subtracting the result of (ii) from the result of (i) to obtain the enhanced image data value.

It is an advantage of the present invention that it has reduced or minimized sensitivity to illumination variation. In other words, the method according to the present invention is a more robust method to generate the FIRE image.

BRIEF DESCRIPTION OF THE DRAWINGS

The above and other features and advantages of the present invention will become more apparent by describing in detail exemplary embodiments thereof with reference to the attached drawings.

DETAILED DESCRIPTION OF THE INVENTION

This invention includes calculation steps. Those skilled in the art will recognize that these calculation steps may be performed by hardware or software. Because image manipulation systems are well known, the present description will be directed in particular to algorithms and systems forming part of, or cooperating more directly with, the method in accordance with the present invention. Other aspects of such algorithms and systems, and hardware and/or software for producing and otherwise processing the image signals involved therewith, not specifically shown or described herein may be selected from such systems, algorithms, components and elements known in the art. Given the description as set forth in the following specification, all software implementation thereof is conventional and within the ordinary skill in such arts.

Still further, as used herein, the software program may be stored in a computer readable storage medium, which may comprise, for example: magnetic storage media such as a magnetic disk (such as a floppy disk) or magnetic tape; optical storage media such as an optical disc, optical tape, or machine readable bar code; solid state electronic storage devices such as random access memory (RAM), or read only memory (ROM); or any other physical device or medium employed to store a computer program.

Before describing the present invention, it facilitates understanding to note that the present invention can be utilized on a computer system, such as a personal computer, or on an embedded system that employs a dedicated data processing component, such as a digital signal processing chip.

Figure 1:
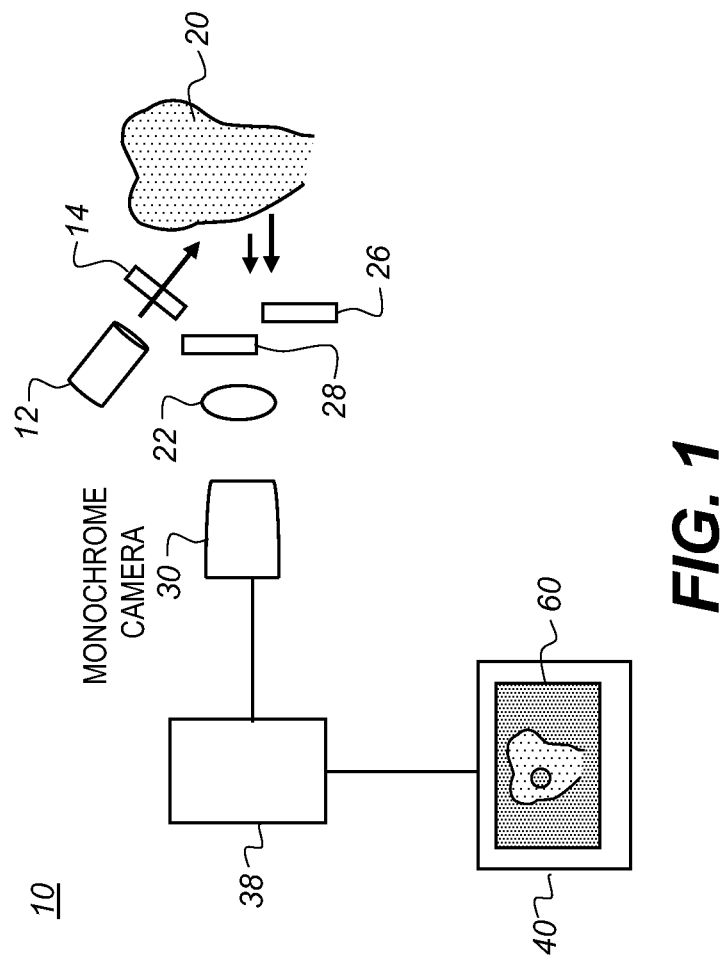
FIG. 1 is a schematic block diagram of an imaging apparatus for caries detection according to the present invention.
Figure 2:
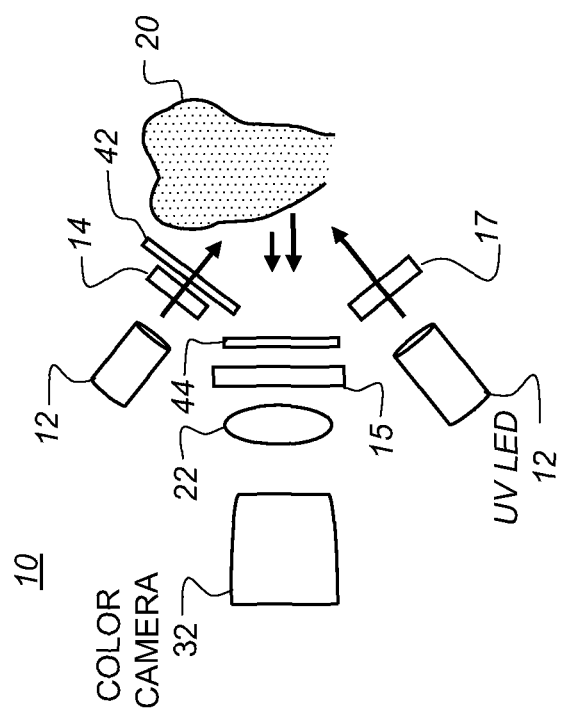
FIG. 2 is a schematic block diagram of an alternate imaging apparatus for caries detection according to the present invention.

With references to FIGS. 1 and 2, the imaging apparatuses, which are described in more detail in the U.S. patent application Ser. No. 11/468,883 and the U.S. patent application Ser. No. 11/530,987, and which are incorporated herein by references, are arranged to perform this invention.

FIG. 1 illustrates an imaging apparatus 10 for caries detection in accordance with the present invention. In FIG. 1, a light source 12 directs an incident light, at a UV-blue wavelength range or other suitable wavelength range, toward tooth 20 through an optional lens 14 or other light beam conditioning component. In practice, light source 12 could emit light ranging in wavelength from an upper ultraviolet range to a deeper blue, between about 300 and 500 nm. The tooth 20 may be illuminated at a smooth surface (as shown) or at an occlusal surface (not shown). Two components of light are then detected by a monochrome camera 30 through a lens 22: a back-scattered light component having the same wavelength as the incident light and having measurable reflectance; and a fluorescent light that has been excited due to the incident light.

Monochrome camera 30 may have color filters 26 and 28. One of color filters 26 or 28 is used during reflectance imaging; the other is used during fluorescence imaging. A processing apparatus 38 obtains and processes the reflectance and fluorescence image data and forms a FIRE image 60. FIRE image 60 is an enhanced image containing caries detection information; it can be printed or can be displayed on a display 40. FIRE image 60 data can also be transmitted to storage or transmitted to another site for display.

FIG. 2 shows an alternate imaging apparatus 10 using a color camera 32 and multiple light sources 12, each light source 12 having a different spectral range. As illustrated, one light source 12 is a white light source for obtaining the reflectance image. The typical spectral range for a white light source can include wavelengths from about 400 to about 700 nm, and it can be emitted from a white LED. The other light source 12 is a UV LED, a blue LED, or other source that emits light having shorter wavelengths for exciting fluorescent emission. For example, its spectral range may be well within 300-500 nm. A band pass filter 17 can be used to narrow the band and reduce optical crosstalk from this second light source into the fluorescence image. A polarizer 42 may be provided in the path of the incident illumination light and an analyzer 44 in the return path of image-bearing light from tooth 20 as a means to minimize the specular reflection component. A long-pass filter 15 in the path of returned light from the tooth is used to attenuate ultraviolet and shorter wavelength visible light (for example, light over the blue portion of the spectrum, centered near about 405+/−40 nm) and to pass longer wavelength light. This arrangement minimizes the effect of blue light that may be used to excite fluorescence (normally centered in the green portion of the spectrum, nominally about 550 nm) and, by attenuating this shorter-wavelength light, allows the use of a white light source as light source 12 for obtaining a reflectance image.

When there are multiple light sources 12, individual light sources 12 can be toggled ON and OFF in order to obtain the corresponding reflectance or fluorescence image at any one time. For the embodiment described with reference to FIG. 2, for example, white light source 12 is ON to obtain the reflectance image (or white light image) at camera 32 or other sensor. The other UV LED source is OFF. Then, when white light source 12 is OFF and the UV LED source is energized, a fluorescence image can be obtained.

Figure 3:
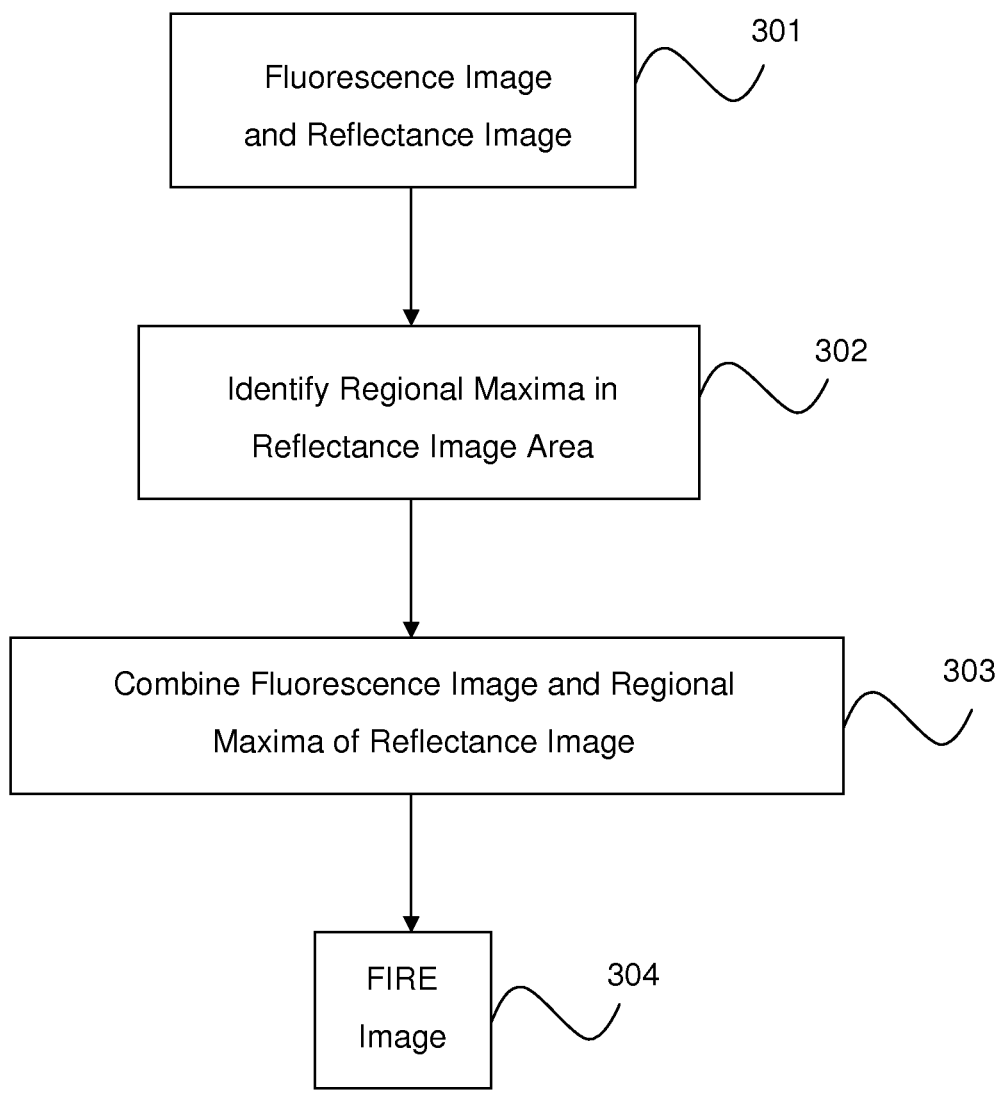
FIG. 3 is a flow chart showing the steps performed in the method of the present invention.

According to the present invention, a method is introduced to generate an improved FIRE image using morphological grayscale reconstruction technique. As shown in FIG. 3, at step 301, fluorescence image data and reflectance image data are captured from the tooth using imaging apparatus 10 diagrammed in FIG. 1 or FIG. 2, in the manner described above. At step 302, regional maxima in the reflectance image are determined. The white spot areas (early caries) on tooth appear brighter than surrounding sound tooth regions in the reflectance image, and they correspond to the regional maxima in the intensity map of the reflectance image, regardless of their absolute pixel values. Therefore, determining regional maxima provides a suitable way of identifying pixels in early caries regions, unaffected by overall variations in image intensity arising from factors such as illumination non-uniformity, imaging optics fall-offs, or tooth geometry. Then, at step 303, the regional maxima of the reflectance image are subtracted from the fluorescence image. The combined image is the FIRE image 304, in which the contrast between caries and sound regions has been enhanced.

Figure 4:
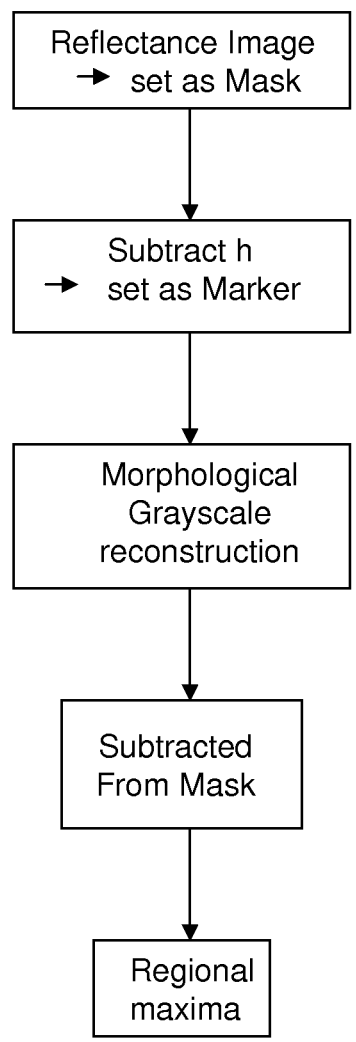
FIG. 4 is a flow chart showing the implementation of step 302 in identifying regional maxima in reflectance image.

A more detailed implementation of step 302 is illustrated in FIG. 4. It makes use of the h-dome transformation image processing technique. H-dome transformation employs a morphological operation, called grayscale reconstruction, and provides a very efficient method to extract regional maxima from grayscale images. H-dome transformation is a suitable technique, even though other morphological procedures employing grayscale reconstruction (such as top-hat by reconstruction) can be similarly used. The methods of grayscale reconstruction and h-dome transformation are useful in many image analysis applications. Since they are well-known, their definition and construction will not be further described here; an extensive discussion can be found in the paper 'Morphological Grayscale Reconstruction in Image Analysis: Applications and Efficient Algorithms' (Published in the IEEE Transactions on Image Processing, Vol. 2, No. 2, pp. 176-201, April 1993). A description is provided here only in the context of how they are applied to regional maxima processing of the reflectance image.

Now referring to FIG. 4, firstly, the reflectance image is set as the Mask. If the reflectance image is a color image, the Mask is a grayscale version of the reflectance image. For example, the Mask can be one color channel of the color image. In the preferred embodiment, the blue color channel of the reflectance image is used as the Mask. Then, the Marker image is calculated from the Mask, by carrying out the following operation:

$$\text{Marker} = \begin{cases} \text{reflectance} - h; & \text{if reflectance} > h \\ 0; & \text{otherwise} \end{cases} \quad (1)$$

where reflectance refers to every pixel value of the Mask, and h is a predetermined value related to the height (in pixel code values) of the regional maxima of interest. For teeth reflectance images with 256 maximum gray levels, h can be in the range of about 40 to about 70. In the preferred embodiment, h is set at 50.

Then, the grayscale reconstruction of the Mask (reflectance) is calculated from the Marker (reflectance-h):

$$\text{Reconstruction Result} = \rho_{reflectance}(\text{reflectance} - h), \quad (2)$$

where $\rho_{reflectance}$ is the morphological grayscale reconstruction operation.

Algorithmic implementations of $\rho_{reflectance}$ are known to those skilled in the image processing art; examples can be found in the reference cited earlier.

Then, the reconstructed image is subtracted from the Mask, to result in the h-dome image $D_h$(reflectance):

$$D_h(\text{reflectance}) = \text{reflectance} - \rho_{reflectance}(\text{reflectance} - h) \quad (3)$$

The h-dome image consists of the regional maxima of the reflectance image, corresponding to the white spot areas of the tooth. It is the image that will be combined with the fluorescence image to generate the FIRE image, in the manner discussed below.

Referring back to FIG. 3, at step 304 the result of the FIRE image is calculated, by employing image fusion to combine the fluorescence image and the h-dome image. Various image fusion techniques can be used. In a preferred embodiment, the h-dome image is subtracted from the fluorescence image to generate FIRE image:

$$\text{FIRE} = \begin{cases} \text{fluorescence} - D_h(\text{reflectance}); & \text{fluorescence} > D_h(\text{reflectance}) \\ 0; & \text{Otherwise} \end{cases} \quad (4)$$

where fluorescence refers to every pixel value of the fluorescence image. If the fluorescence image is a color image, fluorescence refers to every pixel value of a grayscale version of the fluorescence image. In the preferred embodiment, fluorescence refers to every pixel value of the green color channel of the fluorescence image.

Alternatively, scalar multiplications can also be used to adjust the image fusion results. In this case, the FIRE image can be calculated according to the following equation:

$$\text{FIRE} = \begin{cases} m*\text{fluorescence} - n*D_h(\text{reflectance}); & \text{if } m*\text{fluorescence} > n*D_h(\text{reflectance}) \\ 0; & \text{Otherwise} \end{cases} \quad (5)$$

where m and n are scalar multipliers. Depending on the relative intensity of the fluorescence and h-dome images, m and n are chosen to yield optimal contrast in the resultant FIRE image. In the preferred embodiment, m=n=1.

The fusion results, from carrying out the operations of Eqn. (4) or (5), are the FIRE image, which is an enhanced image of the tooth containing desired caries detection information.

As calculated in Equations 4 and 5, the FIRE image is a grayscale image. It can be presented as a grayscale image as is. Alternatively, it can be combined with the red and blue color channels of the fluorescence image to be presented as a composite, color image. The color FIRE image has a greenish appearance, much like the fluorescence image, but with FIRE image content.

Figure 5:
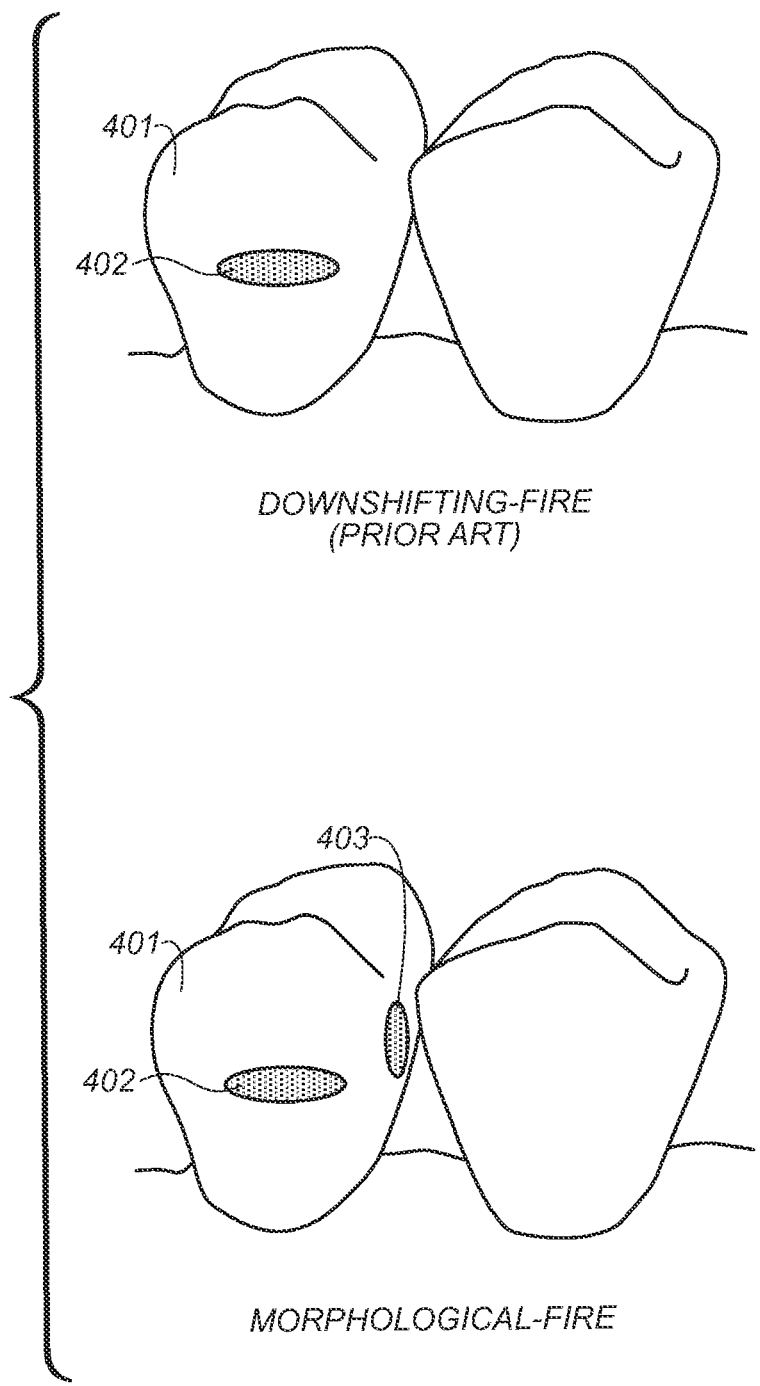
FIG. 5 is an illustrative drawing comparing the downshifting-FIRE image generated according to prior art, and the morphological-FIRE image generated according to the present invention.

The present invention results in pronounced improvement over the downshifting-FIRE implementation in prior art. This is illustrated by the sketch drawing in FIG. 5, which compares the downshifting-FIRE image, generated using prior art, and the morphological-FIRE image, generated using the present invention, for a tooth 401. Lesion 402 near the center of the tooth's buccal surface is detected in both images. However, lesion 403 located closer to the proximal surface, where image intensity is weaker, is missed in the downshifting-FIRE image but clearly detected in the morphological-FIRE image. Consequently, the present invention provides a markedly improved method for FIRE image generation, and offers more sensitive detection of early caries (i.e., white spot lesions).

Alternate Embodiment

Because the regional maxima in the reflectance image directly correspond to slightly demineralized areas on the tooth, the h-dome image itself offers value in early caries detection. This offers an alternate embodiment of caries detection method that uses only the reflectance image. This alternate embodiment does not require fluorescence imaging and FIRE processing, and may be desirable in some situations.

In this alternate embodiment, the imaging apparatuses of FIGS. 1 and 2 can be used as shown, or they can be further simplified by eliminating the UV LED illumination. Reflectance image is captured in the same manner as described previously, and the regional maxima of the reflectance image are obtained by the same process illustrated in FIG. 4. Early caries detection (i.e., white spot lesions) information can then be presented by displaying the h-dome image by itself (with or without image rendering/processing), or by displaying the reflectance image modified by the h-dome image for highlighting the early caries pixels on the tooth. Reflectance image can be modified in many ways, including:

1. Conditioning the pixel values of the reflectance image by those of the h-dome image, such as by an addition operation;

2. Outlining the early caries regions in the reflectance image corresponding to the regional maxima extracted in the h-dome image;
3. Painting false color(s) on pixels in the reflectance image corresponding to the regional maxima extracted in the h-dome image.

It should be noted that the above-mentioned embodiments illustrate rather than limit the invention, and that those skilled in the art will be able to design alternative embodiments without departing from the scope of the appended claims.

In the present specification and claims, use of the verb "to comprise" and "to include", together with their conjugations does not exclude the presence of elements or steps other than those stated therein. The article "a" or "an" preceding an element does not exclude the presence of a plurality of such elements.

What is claimed is:

1. A method for forming an enhanced image of a tooth comprising:
    (a) obtaining fluorescence image data from the tooth by:
        (ai) directing incident light toward the tooth;
        (aii) sensing fluorescent emission from the tooth; and
        (aiii) storing a fluorescence image data value for each pixel position in the fluorescence image data;
    (b) obtaining reflectance image data from the tooth by:
        (bi) directing incident light toward the tooth;
        (bii) sensing back-scattered reflectance light from the tooth; and
        (biii) storing a reflectance image data value for each pixel position in the reflectance image data; and
    (c) combining each pixel in the fluorescence image data with its corresponding pixel in the reflectance image data by:
        (ci) calculating a regional maxima image data value from the reflectance image data; and
        (cii) computing an enhanced image data value according to a difference between the fluorescence image data value and the calculated regional maxima image data value; and whereby the enhanced image is formed from a resulting pixel array of enhanced image data values.

2. The method of claim 1, wherein the wavelength of the incident light for obtaining fluorescence image data is between 300 and 500 nm.

3. The method of claim 1, wherein the incident light is emitted from a white LED in step (b) and the incident light is emitted from a UV LED in step (a).

4. The method of claim 1, wherein the regional maxima image data value is calculated based on a morphological procedure employing grayscale reconstruction.

5. The method of claim 4, wherein the morphological procedure is h-dome transformation, and comprises the following steps:
    (1) calculating a Marker image from the Mask, which is a grayscale version of the reflectance image, by subtracting a predetermined value from the Mask;
    (2) calculating the grayscale reconstruction of the Mask from the Marker; and
    (3) calculating the regional maxima image data value by subtracting the result of (2) from the Mask.

6. The method of claim 5, wherein the predetermined value is in the range of 40 to 70.

7. The method of claim 1, wherein the enhanced image data value computing step is performed by subtracting the regional maxima image data value from the fluorescence image data value.

8. The method of claim 1, wherein the enhanced image data value computing step is performed by:
    (i) multiplying the fluorescence image data value by a first scalar multiplier;
    (ii) multiplying the regional maxima image data value by a second scalar multiplier; and
    (iii) subtracting the result of (ii) from the result of (i) to obtain the enhanced image data value.

9. A method for forming an image of a tooth for caries detection comprising:
    a) obtaining reflectance image data from the tooth by:
    (ai) directing incident light toward the tooth; and
    (aii) sensing back-scattered reflectance light from the tooth;
    (aiii) storing a reflectance image data value for each pixel position in the reflectance image data; and
    b) calculating a regional maxima image data value from the reflectance image data.

10. The method of claim 9 further comprising the step of displaying the regional maxima image data value or a processed regional maxima image.

11. The method of claim 9 further comprising the step of modifying the reflectance image by the regional maxima image to generate a modified reflectance image.

12. The method of claim 11 further comprising the step of displaying the modified reflectance image.

13. The method of claim 11 wherein the step of modifying the reflectance image comprises the step of conditioning the pixel values of the reflectance image by the corresponding pixel values of the regional maxima image.

14. The method of claim 11 wherein the step of modifying the reflectance image comprises the step of outlining the regions in the reflectance image corresponding to the regional maxima in the regional maxima image.

15. The method of claim 11 wherein the step of modifying the reflectance image comprises the step of painting false color(s) on pixels in the reflectance image corresponding to the regional maxima in the regional maxima image.

16. The method of claim 9, wherein the regional maxima image is calculated based on a morphological procedure employing grayscale reconstruction.

17. The method of claim 16, wherein the morphological procedure is h-dome transformation, which comprises the following steps:
    (1) calculating a Marker image from the Mask, which is a grayscale version of the reflectance image, by subtracting a predetermined value from the Mask;
    (2) calculating the grayscale reconstruction of the Mask from the Marker image; and
    (3) calculating the regional maxima image data value by subtracting the result of (2) from the Mask.

18. The method of claim 17, wherein the predetermined value is in the range of 40 to 70.

19. An apparatus for forming an enhanced image of a tooth comprising:
    means for obtaining fluorescence image data from the tooth by:
        (ai) directing incident light toward the tooth;
        (aii) sensing fluorescent emission from the tooth; and
        (aiii) storing a fluorescence image data value for each pixel position in the fluorescence image data;
    means for obtaining reflectance image data from the tooth by:
        (bi) directing incident light toward the tooth;
        (bii) sensing back-scattered reflectance light from the tooth; and (biii) storing a reflectance image data value for each pixel position in the reflectance image data; and means for combining each pixel in the fluorescence image data with its corresponding pixel in the reflectance image data by:
   (ci) calculating a regional maxima image data value from the reflectance image; and
   (cii) computing an enhanced image data value according to a difference between the fluorescence image data value and the regional maxima image data value; and whereby the enhanced image is formed from a resulting pixel array of enhanced image data values.

20. An apparatus for forming an image of a tooth for caries detection comprising:

means for obtaining reflectance image data from the tooth by:

(ai) directing incident light toward the tooth; and (aii) sensing back-scattered reflectance light from the tooth;

(aiii) storing a reflectance image data value for each pixel position in the reflectance image data; and means for calculating a regional maxima image data value from the reflectance image data.

\* \* \* \* \*